United States Patent
Preis (10) Patent No.: US 10,368,722 B2
(45) Date of Patent: Aug. 6, 2019

(54) ENDOSCOPIC INSTRUMENT AND ENDOSCOPIC INSTRUMENT SYSTEM

(71) Applicant: Karl Storz SE & Co. KG, Tuttlingen (DE)

(72) Inventor: Fridolin Preis, Hattingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 69 days.

(21) Appl. No.: 14/959,123

(22) Filed: Dec. 4, 2015

(65) Prior Publication Data

US 2016/0157701 A1 Jun. 9, 2016

(30) Foreign Application Priority Data

Dec. 5, 2014 (DE) .................. 10 2014 118 003

(51) Int. Cl.
*A61B 1/04* (2006.01)
*A61B 1/00* (2006.01)
(Continued)

(52) U.S. Cl.
CPC ........ *A61B 1/00087* (2013.01); *A61B 1/0011* (2013.01); *A61B 1/00071* (2013.01); *A61B 1/00119* (2013.01); *A61B 1/00121* (2013.01); *A61B 1/00135* (2013.01); *A61B 1/00163* (2013.01); *A61B 1/015* (2013.01); *A61B 1/018* (2013.01); *A61B 10/04* (2013.01); *A61B 10/06* (2013.01); *A61B 17/29* (2013.01); *A61B 17/3421* (2013.01); *A61B 1/121* (2013.01); (Continued)

(58) Field of Classification Search
CPC .......................... A61B 1/00142; A61B 1/00154

USPC ................. 600/104–107, 121–125, 153–159
See application file for complete search history.

(56) References Cited

U.S. PATENT DOCUMENTS 4,726,370 A * 2/1988 Karasawa ............... A61B 18/14
600/105
5,025,778 A * 6/1991 Silverstein ........... A61B 1/0008
600/104

(Continued)

FOREIGN PATENT DOCUMENTS

DE 10129990 B4 3/2004
DE 60035936 T2 12/2007
(Continued)

OTHER PUBLICATIONS

European Search Report Application No. 15192242.4 dated Apr. 6, 2016 9 pages.
(Continued)

*Primary Examiner* — Matthew J Kasztejna
(74) *Attorney, Agent, or Firm* — Whitmyer IP Group LLC (57) ABSTRACT

An endoscopic instrument according to the invention includes an elongate tube, which has an axially continuous and substantially cylindrical main lumen for receiving a shaft of an endoscope lens system, and a tool, which is arranged at a distal end of the tube and can be controlled via an elongate transmission element from a proximal end of the tube, wherein the tube has an axially continuous secondary lumen which adjoins the main lumen in a transverse direction, is connected to the main lumen via a narrowed transition area and receives the transmission element. The invention also relates to an endoscopic instrument system.

18 Claims, 4 Drawing Sheets

(51) Int. Cl.
*A61B 1/018* (2006.01)
*A61B 10/04* (2006.01)
*A61B 1/015* (2006.01)
*A61B 10/06* (2006.01)
*A61B 17/29* (2006.01)
*A61B 17/34* (2006.01)
*A61B 1/12* (2006.01)
*A61B 18/00* (2006.01)
*A61B 17/02* (2006.01)
*A61B 17/00* (2006.01)
*A61B 90/00* (2016.01)

(52) U.S. Cl.
CPC ... *A61B 17/0218* (2013.01); *A61B 2017/0046* (2013.01); *A61B 2017/00296* (2013.01); *A61B 2017/00331* (2013.01); *A61B 2018/00982* (2013.01); *A61B 2090/0813* (2016.02)

(56) References Cited

U.S. PATENT DOCUMENTS

| | | | |
|---|---|---|---|
| 5,392,765 A | 2/1995 | Muller | |
| 5,503,616 A * | 4/1996 | Jones | A61B 1/00135 |
| | | | 600/121 |
| 5,549,541 A | 8/1996 | Muller | |
| 5,749,889 A * | 5/1998 | Bacich | A61B 17/3417 |
| | | | 600/104 |
| 5,820,630 A * | 10/1998 | Lind | A61B 10/06 |
| | | | 606/205 |
| 5,855,569 A * | 1/1999 | Komi | A61B 10/04 |
| | | | 604/103 |
| 6,071,233 A * | 6/2000 | Ishikawa | A61B 1/0014 |
| | | | 600/104 |
| 6,878,106 B1 * | 4/2005 | Herrmann | A61B 1/00073 |
| | | | 600/104 |
| 7,056,284 B2 * | 6/2006 | Martone | A61B 1/00071 |
| | | | 600/121 |
| 7,794,393 B2 * | 9/2010 | Larsen | A61B 1/12 |
| | | | 600/105 |
| 8,277,373 B2 * | 10/2012 | Maahs | A61B 1/0008 |
| | | | 600/104 |
| 8,602,970 B2 * | 12/2013 | Muyari | A61B 1/00087 |
| | | | 600/104 |
| 9,486,125 B2 * | 11/2016 | James | A61B 1/00135 |
| 2001/0056222 A1 | 12/2001 | Rudischhauser et al. | |
| 2002/0120180 A1 * | 8/2002 | Speier | A61B 1/00135 |
| | | | 600/125 |
| 2003/0195387 A1 * | 10/2003 | Kortenbach | A61B 1/00073 |
| | | | 600/104 |
| 2004/0230095 A1 * | 11/2004 | Stefanchik | A61B 1/00073 |
| | | | 600/104 |
| 2005/0234298 A1 * | 10/2005 | Kucklick | A61B 1/00135 |
| | | | 600/156 |
| 2007/0173687 A1 * | 7/2007 | Shima | A61B 1/018 |
| | | | 600/106 |
| 2010/0016659 A1 * | 1/2010 | Weitzner | A61B 1/00073 |
| | | | 600/104 |
| 2010/0145142 A1 | 6/2010 | Begemann et al. | |
| 2012/0035416 A1 | 2/2012 | Fernandez et al. | |
| 2012/0157772 A1 * | 6/2012 | James | A61B 1/00135 |
| | | | 600/156 |
| 2012/0289858 A1 | 11/2012 | Ouyang et al. | |
| 2014/0288460 A1 | 9/2014 | Ouyang et al. | |

FOREIGN PATENT DOCUMENTS

| | | |
|---|---|---|
| DE | 102010054422 A1 | 6/2012 |
| DE | 202012006159 U1 | 8/2012 |
| EP | 0455188 A2 | 11/1991 |

OTHER PUBLICATIONS

German Search Report Application No. DE 10 2014 118 003.8 dated Jul. 17, 2015; Received: Jul. 28, 2015 8 pages.

* cited by examiner

ENDOSCOPIC INSTRUMENT AND ENDOSCOPIC INSTRUMENT SYSTEM

FIELD OF THE INVENTION

The present invention relates to an endoscopic instrument and system.

BACKGROUND OF THE INVENTION

Endoscopic operating techniques have become widely used in a large number of surgical or diagnostic procedures. In these procedures, an endoscopic instrument system, which in particular comprises an endoscope lens system and an endoscopic instrument, is guided through a natural opening of the body, or through an artificial opening created with the aid of an incision, to a target site located inside the body, particularly in a cavity inside the body, where the surgical or diagnostic procedure is to be performed. In many uses, it has proven advantageous to guide a rigid outer shaft through the body opening into the cavity, wherein the interior of the outer shaft receives a rigid endoscope lens system and an endoscopic instrument and also, if appropriate, further channels which can serve, for example, for the introduction of further instruments or as irrigation channels.

An endoscope lens system, often also designated as an "endoscope", typically has, in the case of a rigid endoscope lens system, a rigid and elongate cylindrical shaft in the distal end area of which, i.e. in the area directed away from the user, an endoscope objective lens is arranged for generating an endoscopic image of the target site. The endoscopic image generated is typically carried through an image carrier, arranged inside the shaft, to the proximal end of the endoscope lens system, i.e. the end near the user. Since there is generally insufficient light in the cavity, a light-guiding system composed of optical fibers is also usually arranged inside the shaft of the endoscope lens system, in order to transport sufficient light to the distal end of the endoscope lens system, where it is used to illuminate the target site.

An endoscopic instrument designed for use in an endoscopic instrument system of said type commonly has an elongate tube which is designed to receive the shaft of the endoscope lens system. A tool for carrying out endoscopic manipulations is arranged at the distal end of the tube, which tool can be controlled, via an elongate transmission element, from the proximal end of the tube, for example by means of a handle arranged at the proximal end. The handle and the proximal end of the endoscope lens system remain outside the body opening during the endoscopic procedure, while the outer shaft, the tube with the tool and the shaft of the endoscope lens system are guided to the target site. The necessary effective length of the outer shaft and of the endoscope lens system and of the tube with the tool is dependent in particular on the nature of the endoscopic procedure and on the access route used.

A cystoscope comprising an outer shaft and an inner element is known from U.S. Pat. Nos. 5,392,765 and 5,549,541, wherein the inner element is positioned in a central cavity of the outer shaft and has an inner channel which comprises a first passage, adapted to receive an endoscope lens system, and a second passage, which is used for guiding a laser fiber. Further areas of the inner channel serve for the conveying of irrigation liquid. The guiding of the laser fiber is not always satisfactory.

An endoscopic instrument for use in an endoscopic instrument system of the type mentioned at the outset is sold by Karl Storz GmbH & Co. KG under the name 10377 HF. The tube for receiving the cylindrical shaft of the endoscope lens system is likewise cylindrical. A tool designed in the form of forceps is arranged at the distal end of the tube, which tool can be actuated by means of a handle, arranged at the proximal end to the tube, via a transmission element designed as a pull rod. The forceps are located in the viewing field of an endoscope lens system guided through the tube, and they thus allow endoscopic manipulations performed with the forceps to be monitored endoscopically; such an instrument is therefore also designated by the expression "optical forceps". The pull rod is guided in a guide tube extending parallel to the tube, which guide tube extends parallel to the tube and is welded to the outside of the latter. The production of a tube of this type with a welded-on guide tube is relatively complicated and costly.

The endoscope lens system and the tube, the tool and the outer shaft are often provided for repeated use. Therefore, after a surgical intervention, the endoscopic instrument system has to be cleaned and sterilized before being used again. To clean the tube, it is known to flush a cleaning liquid through it. The cleaning of the guide tube is associated with a relatively high cost.

SUMMARY OF THE INVENTION

The object of the present invention is to make available an endoscopic instrument of said type and also an endoscopic instrument system having such an endoscopic instrument, wherein the abovementioned disadvantages are avoided as far as possible, in particular with production and cleaning being improved.

This object is achieved by an endoscopic instrument and by an endoscopic instrument system according to the invention.

Advantageous developments of the invention are set forth in the dependent claims.

An endoscopic instrument according to the invention comprises an elongate tube, which has an axially continuous lumen, i.e. a continuous inner cavity. The lumen comprises two likewise axially continuous and interconnected sub-regions. A first sub-region is designed to receive a shaft of a rigid endoscope lens system. This sub-region or this sub-lumen preferably occupies most of the continuous cavity of the tube and is therefore designated below as the main lumen. Since the shaft of a rigid endoscope lens system is generally cylindrical, in particular circularly cylindrical, the main lumen is likewise substantially cylindrical, in particular circularly cylindrical. The main lumen reaches from a proximal end to a distal end of the tube. An endoscope lens system which is inserted into the main lumen of the tube, and of which the shaft is slightly longer than the tube, can therefore be pushed forward in such a way that the distal end of the endoscope lens system protrudes from the distal end of the tube and, at the same time, the proximal end area of the endoscope lens system, which can have an attachment piece for the attachment of a fiber optic cable and a camera attachment or an eyepiece, remains outside the tube at the proximal end thereof. The length of the tube, or the length of the shaft of the endoscope lens system, depends on the effective length needed for the endoscopic procedure that is to be performed.

The endoscopic instrument according to the invention furthermore comprises an endoscopic tool which is arranged at a distal end of the tube and in particular is connected to a distal end area of the tube. The tool can be connected to the tube either permanently or releasably. The tool can be controlled via an elongate transmission element from the proximal end of the tube. The transmission element can be designed as a mechanical transmission element for transmitting a mechanical action, i.e. in particular for transmitting a force or a movement, for example a pulling or pushing force or movement, although it can also be designed, for example, as a laser fiber for the transmission of optical energy. The transmission element can be a constituent part of the endoscopic instrument and can be connected to the latter either permanently or releasably. Depending on the nature of the tool, the transmission element is connected or connectable thereto either rigidly or in an articulated manner.

According to the invention, the tube has an axially continuous further sub-lumen which adjoins the main lumen in a first transverse direction to the axial direction and which forms a further sub-region of the continuous cavity of the tube. This sub-lumen preferably has a smaller cross-sectional area than the main lumen and laterally adjoins the main lumen and is therefore designated below as a secondary lumen. The secondary lumen can be substantially cylindrical, in particular circularly cylindrical. The secondary lumen is connected to the main lumen via a transition area, which is narrowed in relation to the main lumen and the secondary lumen. The axially continuous cavity can in particular be designed in such a way that the main lumen and the secondary lumen are each circular in cross section with different diameters, but in each case with omission of a circle portion, and the transition area is formed in cross section by the two omitted, mutually facing circle portions and by an area connecting these. The transition area is in particular narrowed in a second transverse direction perpendicular with respect to the axial direction and to the first transverse direction, i.e. a minimal clearance of the transition area measured in the second transverse direction is smaller than the maximum clearance of the secondary lumen and of the main lumen measured in the same direction. The secondary lumen receives the elongate transmission element and is therefore preferably likewise designed to be continuous from the proximal end to the distal end of the tube.

The endoscopic instrument is suitable in particular for insertion into an outer shaft, which is designed to be inserted through a natural or artificial opening of the body into a cavity inside the body. A handle, for example, is arranged or can be arranged at the proximal end of the tube, which handle can have an actuation element for actuating the tool, which actuation element for this purpose is connected or connectable to the transmission element and permits the actuation of a tool provided with a movable tool element. Moreover, a mechanism for fixing or locking an endoscope lens system inserted into the tube and/or a mechanism for fixing or locking in an outer shaft, into which the tube has been inserted, can be arranged in the proximal end area of the tube. The endoscopic instrument can be designed, for example, for use with a bronchoscope, an esophagoscope, a cystoscope or a uretero-renoscope.

By virtue of the fact that the tube comprises an axially continuous secondary lumen, which laterally adjoins the main lumen and is connected thereto via a transition area and serves to receive the transmission element, it is possible, when flushing the main lumen with a cleaning liquid, at the same time to flush the secondary lumen and thereby clean the secondary lumen in a simple and safe way. Moreover, by virtue of the fact that the lumen of the tube has a main lumen for receiving the shaft of the endoscope lens system and a secondary lumen for receiving the transmission element for controlling the tool, it is possible to omit the provision of a guide tube for the transmission element. In this way, it is possible to make savings in terms of material costs and processing costs. Finally, by virtue of the fact that the transition area between the secondary lumen and the main lumen is narrowed, it is possible for the transmission element to be guided in the secondary lumen, as a result of which the insertion of the transmission element upon assembly of the endoscopic instrument is made easier, and the mode of operation of the transmission element during use of the endoscopic instrument is improved.

Preferably, the endoscopic instrument comprises only a single secondary lumen and only a single transition area between the secondary lumen and the main lumen. In this way, an embodiment is created which is particularly simple and inexpensive to produce and which is safe to use and to clean. However, it is also conceivable that the endoscopic instrument has more than one secondary lumen, in which case preferably each secondary lumen is connected to the main lumen via a respective narrowed transition area. In this way, an endoscopic instrument is created which provides extended functionality, for example by use of several tools that can be controlled from the proximal end via a respective transmission element, which is received in a respective secondary lumen.

The tube is preferably designed as a profiled tube made of a metal, for example stainless steel, with a non-circular cross section or a non-circular lumen. A profiled tube of this kind is preferably produced without joints, for example by extrusion and/or drawing. Simple and cost-effective production of the tube is permitted in this way.

According to a preferred embodiment of the invention, the tube is designed with a substantially uniform wall thickness. Therefore, according to this embodiment, the wall thickness of the tube, if appropriate apart from a proximal and/or a distal end portion, is uniform in each cross section along the circumference in question. Cross sections that are mutually offset in the axial direction can have different wall thicknesses; however, the tube preferably has the same uniform wall thickness in all cross sections, wherein the wall thickness may deviate at the distal end and/or proximal end, for example in order to define a distal end stop for the endoscope lens system and/or to secure a latching mechanism. Particularly advantageously, the tube is designed as a profiled tube made of metal, for example stainless steel, with a lumen of non-circular cross section and with a uniform wall thickness. This permits particularly cost-effective production and a favorable utilization of space.

Preferably, the narrowed transition area is axially continuous at least as far as a proximal end area of the tube. The secondary lumen is thus connected to the main lumen along substantially the entire length of the tube. By virtue of the fact that the secondary lumen is connected axially continuously to the main lumen, the irrigation of the secondary lumen with cleaning liquid during an irrigation of the main lumen is further improved.

It is furthermore preferable that the constriction of the transition area is narrower than the corresponding transverse dimension of the transmission element, i.e. that a minimal clearance of the transition area is smaller than the maximum width of the transmission element measured in a corresponding direction, which can be the second transverse direction perpendicular to the first transverse direction and to the axial direction. In the case where the transmission element is cylindrical, the constriction of the transition area is therefore narrower than corresponds to the diameter of the transmission element. In this way, the transmission element can be reliably prevented from moving from the secondary lumen into the main lumen. The assembling of the instrument and the guiding of the transmission element are thus further improved.

According to a preferred embodiment of the invention, the transmission element is guided in the secondary lumen at a distance from the main lumen, such that, when the shaft of an endoscope lens system is inserted into the main lumen, the transmission element is held at a distance from the shaft of the endoscope lens system. In particular, the transition area is dimensioned such that the transmission element is at a distance, in the first transverse direction, from a cylindrical shaft of an endoscope lens system which is inserted into the main lumen and which practically fills the cross section thereof. In this way, it is possible to safely avoid contact and resulting friction between the shaft of the endoscope lens system and the transmission element, and the control of the tool via the transmission element can thus be further improved. This is particularly advantageous in the case where the transmission element for controlling a tool with at least one movable tool element is guided movably, for example longitudinally displaceably, in the secondary lumen.

Particularly preferably, the transmission element is guided in the secondary lumen with such a clearance that a distance from the inner wall of the tube remains that is sufficient for irrigation of the secondary lumen with cleaning liquid. For this purpose, a sufficient distance between the transmission element and the inner wall of the tube may be from one to several tenths of a millimeter. The cleaning of the secondary lumen, in which the transmission element extends, and of the transmission element itself is further facilitated in this way.

The tool, which is arranged at the distal end of the tube, can be designed, for example, as a pair of forceps or scissors, a punch, an expansible and retractable collecting basket or the like. Preferably, the tool comprises at least one movable tool element which can be actuated via the transmission element, for which purpose the transmission element can be designed as a pull rod or pull wire. The pull rod can advantageously be suitable not only for applying a pulling force but also, at least to a limited extent, for applying a pressing or pushing force. For simplicity, a pulling/pushing element of this kind is likewise designated below as a "pull rod". By virtue of the fact that the tool comprises at least one movable tool element which can be actuated by means of the transmission element designed as a pull rod, a use of the endoscopic instrument is permitted for a large number of endoscopic manipulations. Particularly advantageously, use can be made of the fact that the pull rod according to the abovementioned design of the tube can be guided at a distance from an inserted endoscope lens system, thereby permitting reliable actuation of the movable tool element and the application of high pulling and/or pushing forces to the latter. Alternatively, the transmission element can be designed, for example, as an optical fiber for transmitting laser radiation from the proximal end to the distal end area of the endoscopic instrument, wherein the tool is a distal end area of the optical fiber with an exit surface for the laser radiation for treatment of tissue.

According to a particularly preferred embodiment of the invention, the tool is designed as forceps or scissors and comprises at least one pivotable tool element. The latter is a forceps jaw part or scissor blade and is mounted so as to be pivotable about a transverse stub lying substantially transverse to the longitudinal axis of the tube. For this purpose, the transverse stub can be connected to a distal end area of the tube via a holder, wherein the pull rod is connected or connectable to the at least one pivotable forceps jaw part of scissor blade in an articulated manner. By actuating an actuation element of a handle arranged at the proximal end of the endoscopic instrument, it is possible for the pull rod to be moved relative to the tube in the axial direction and, in this way, for the tool element to be pivoted. Particularly advantageously, the tool comprises two pivotable jaw parts or scissor blades which act against each other and which are each connected to the distal end of the pull rod in an articulated manner, for example via a respective lever. In this way, a versatile endoscopic instrument is created which is easy and safe to actuate and which allows a large number of tissue manipulations to be performed in a cavity inside the body or also permits the excision of samples or the removal of foreign bodies under endoscopic monitoring.

It is furthermore preferable that a proximal end area of the tube has an attachment piece for the introduction of a cleaning liquid. This attachment piece can be arranged, for example, at the proximal end of the main lumen and can be provided with a coupling mechanism for attachment to a corresponding attachment piece of a medical irrigation machine. Particularly preferably, the attachment piece is designed in such a way that cleaning liquid can be introduced through the proximal opening of the main lumen and thus via a large cross section into the tube. The coupling mechanism can be combined with a latching mechanism for fixing an endoscope lens system inserted into the tube, or the coupling mechanism can at the same time have the function of the latching mechanism. The cleaning liquid enters the tube via the proximal end and preferably exits again at the distal end, wherein the main lumen and the secondary lumen, if appropriate together with the transmission element received in the secondary lumen, are cleaned. In this way, the cleaning of the endoscopic instrument is further simplified. The liquid introduced can also serve for the sterilization of the endoscopic instrument.

An endoscopic instrument system according to the invention comprises an endoscopic instrument designed as described above. Furthermore, the endoscopic instrument system comprises a rigid endoscope lens system, which can be inserted into the main lumen of the tube. The main lumen and the shaft of the endoscope lens system are preferably adapted to each other in such a way that the endoscope lens system is guided with slight play in the main lumen, wherein the shaft of the endoscope lens system is slightly longer than the tube. The endoscope lens system can therefore be inserted into the tube in such a way that the distal end of the endoscope lens system comes to lie in the area of the distal end of the tube or protrudes a short distance from the latter, for example by about one or a few centimeters, in order to permit an as far as possible unobstructed endoscopic view of the tool. The shaft of the endoscope lens system preferably has a circular cylindrical shape.

Moreover, the endoscopic instrument system can comprise an outer shaft into which the endoscopic instrument can be inserted and which for this purpose has a corresponding continuous cavity. The length of the outer shaft is chosen such that the tool of the endoscopic instrument protrudes from a distal opening of the outer shaft and can be controlled by an actuation element or supply element arranged at the proximal end of the outer shaft. The outer shaft has in particular an atraumatic design and can, for example, have a lip raised on one side above the distal opening and creating a viewing and working space for the endoscope lens system and the tool. The outer shaft can, for example, have a circular or oval cross section, or also a cross section formed by two semicircles with straight parts lying between these, wherein a remaining space between the tube of the endoscopic instrument inserted into the outer shaft serve for irrigation of an operating site, in which endoscopic manipulations are performed with the tool of the endoscopic instrument, or also for receiving further endoscopic tools.

The endoscopic instrument system can comprise further components, for example further tools, irrigation attachments, supply devices for providing illumination light, irrigation liquid or electrical energy or light energy for the endoscopic tool, and also display and evaluation devices for a recorded endoscopic image.

When performing an endoscopic procedure with the endoscopic instrument system according to the invention, an endoscope lens system is inserted into the endoscopic instrument, which comprises the tool, and is fixed in a position therein such that the tool can be observed with the endoscope lens system. A handle, which cooperates with the transmission element received in the tube in order to actuate the tool, may have been fastened beforehand to the proximal end area of the tube. The endoscopic instrument with the endoscope lens system is inserted into an outer shaft and is fixed in a suitable position in which, for example, an atraumatic lip protrudes sufficiently far from the distal end of the endoscope lens system in order to create a viewing and working space. The outer shaft is then inserted, with the endoscopic instrument and the endoscope lens system, through a body opening to the target site, where the endoscopic procedure is to be performed. Said steps can also take place in another sequence or, if appropriate, after insertion of the outer shaft through the body opening. After completion of the procedure, the outer shaft is withdrawn from the body opening and the endoscopic instrument and the endoscope lens system are each released and removed from the outer shaft or the tube; these steps too may optionally be carried out in a different sequence. By way of preparation, the main lumen of the endoscopic instrument is exposed to cleaning liquid, which penetrates into the secondary lumen and likewise flushes through the latter. For this purpose, an irrigation attachment piece of the endoscopic instrument is preferably connected to a corresponding attachment piece of a medical irrigation machine, and the endoscopic instrument is cleaned in this. The outer shaft and the endoscope lens system, and if appropriate the handle, are cleaned in the usual way. Moreover, sterilization takes place in a known manner, for example by autoclaving.

It will be appreciated that the aforementioned features, and the features still to be explained below, can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which.

DETAILED DESCRIPTION OF THE INVENTION

Figure 1:
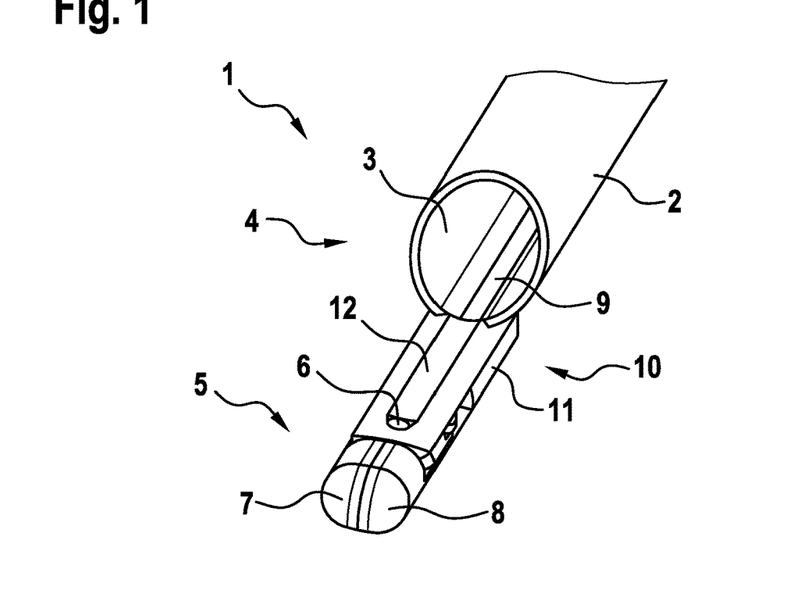
FIG. 1 shows the distal end area of an endoscopic instrument according to a first illustrative embodiment of the invention, in a perspective view.

In FIG. 1, the distal end area of an endoscopic instrument 1, designed according to a first illustrative embodiment of the invention, is shown in a view seen obliquely from the distal direction. The endoscopic instrument 1 has a tube 2, which encloses a continuous and substantially cylindrical cavity, which is here designated as main lumen 3. At the distal end, the main lumen 3 opens out in an opening arranged obliquely with respect to a longitudinal axis of the tube 2. The tool designed as forceps 5, for example as gripping forceps or biopsy forceps, is arranged at the distal end 4 of the tube 2. The forceps 5 comprise two interacting jaw parts 7, 8 which are pivotable about a transverse stub 6 and which are each connected in an articulated manner to a pull rod 9 that extends under the main lumen 3. The transverse stub 6 is held on the distal end area of the tube 2 by a holder designed as a fork 10. The fork 10 is composed of a main part 11 which encloses the joint mechanism (not shown in detail in FIG. 1), via which the jaw parts 7, 8 are connected to the pull rod 9, and into which the transverse stub 6 is inserted. In the proximal direction, the transverse stub 6 is supported by the insert 12. The main part 11 of the fork 10 can be designed in one or more parts. The fork 10, at least the main part 11, is secured to the distal end area of the tube 2 by welding.

Figure 2:
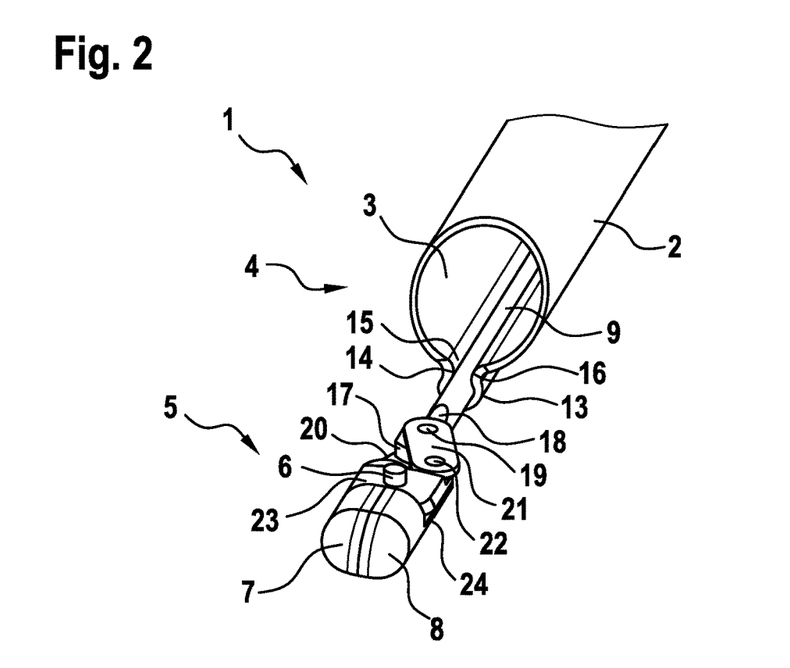
FIG. 2 shows the endoscopic instrument from FIG. 1, but without the holder of the tool.

As is shown in FIG. 2, in a view corresponding to FIG. 1 but with the fork 10 omitted, the tube 2 is designed as a profiled tube which has a non-circular cross section and, below the continuous and substantially cylindrical main lumen 3, encloses a secondary lumen 14 formed by the convexity 13, which secondary lumen 14 is likewise axially continuous and accommodates the pull rod 9. In a transition area 15 between the main lumen 3 and the secondary lumen 14, the wall of the tube 2 forms a constriction 16, the clear width of which is smaller than the diameter of the cylindrical pull rod 9, such that the latter is held and securely guided inside the secondary lumen 14. The secondary lumen 14 is partially cylindrical, wherein the radius of the cylinder is chosen such that a space remains between the pull rod 9, received in the secondary lumen 14, and the wall of the tube 2 in the area of the convexity 13, which space permits not only a low-friction longitudinal displaceability of the pull rod 9, but also the passage of cleaning liquid between the pull rod 9 and the wall of the tube 2. The distal opening of the tube 2 is substantially perpendicular to the longitudinal axis of the tube 2 in the area of the convexity 13.

The distal end of the pull rod 9 is formed by a plate 17, wherein the transition from the cylindrical cross section of the pull rod 9 to the plate 17 is provided by a bevel 18. The plate 17 is adjoined on both sides by a respective lever 20, 21, which is mounted in an articulated manner with an axial pin 19. The levers 20, 21 are in turn each connected via a respective axial pin 22 to a respective plate-shaped bearing portion 23, 24 of the jaw parts 7, 8. The jaw parts 7, 8 are mounted pivotably on the transverse stub 6 by means of their bearing portions 23, 24. Since the transverse stub 6 is held at the distal end of the tube 2, the jaw parts 7, 8 can be spread apart and closed again by a longitudinal movement of the pull rod 9.

Figure 3:
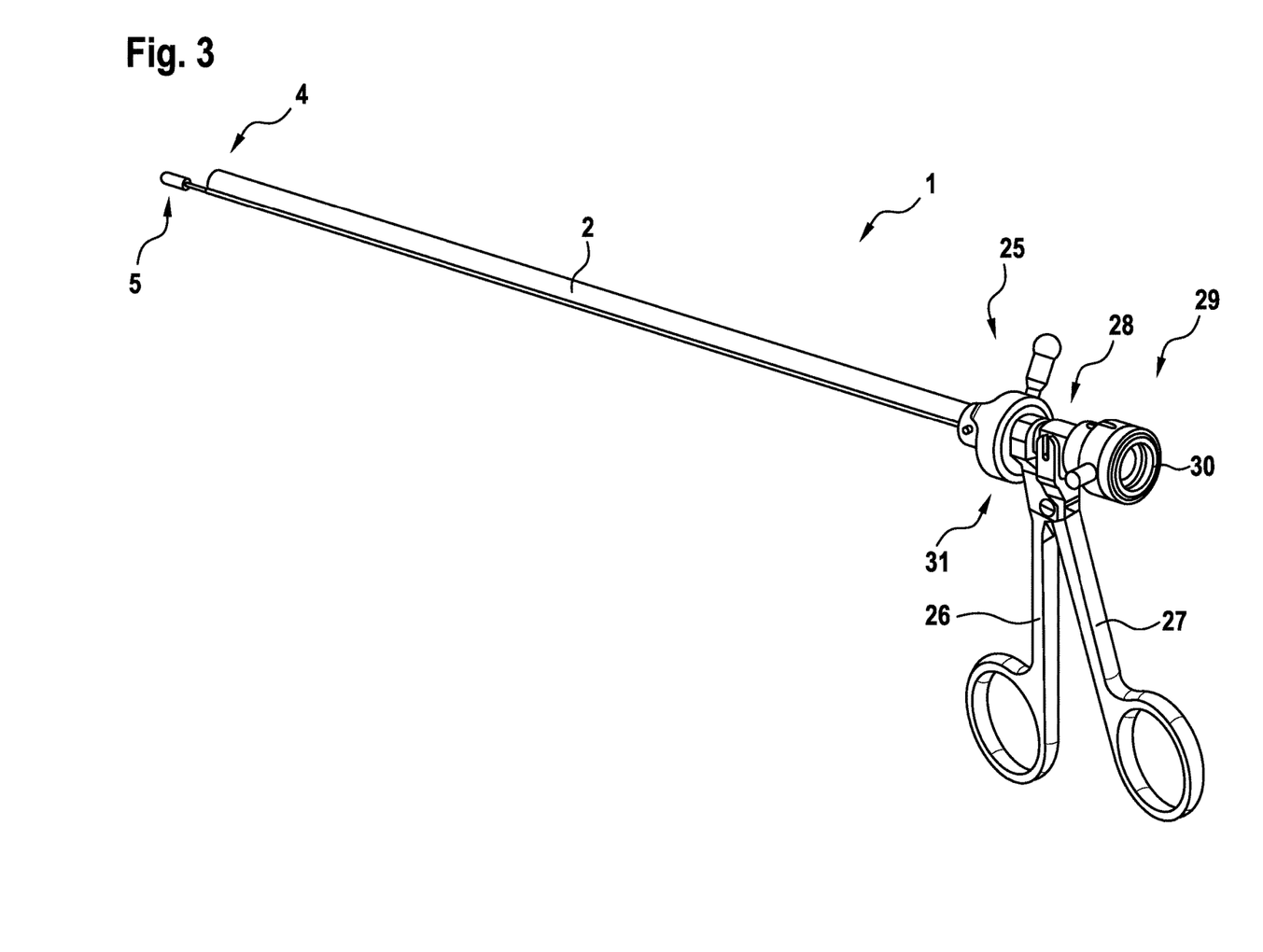
FIG. 3 shows the endoscopic instrument from FIG. 2 in an overall view with an attached handle.

As is shown in FIG. 3 in a view of the endoscopic instrument 1 seen obliquely from the proximal direction, a handle can be mounted on the proximal end 25 of the tube 2 of the endoscopic instrument 1 in order to permit the longitudinal movement of the pull rod 9 and, consequently, the actuation of the jaw parts 7, 8 of the forceps 5. The handle is composed of a stationary grip part 26, which is releasably connected to the tube 2, and of a grip part 27 which is mounted pivotably with respect to the stationary grip part 26. The grip part 27 is connected to the proximal end area of the pull rod 9 via a releasable connection mechanism 28 (see FIG. 2). To make handling easier, the grip parts 26, 27 each have a grip ring. It will also be seen from FIG. 3 that, in the proximal end area of the tube 2, a first latching mechanism 29 is arranged which encloses a proximal continuation of the main lumen 3 (see FIGS. 1 and 2) and with the aid of which an endoscope lens system inserted into this and into the main lumen 3 of the tube 2 is secured and can be locked in a suitable position (see FIG. 4). The proximal opening of the continuation of the main lumen 3 serves at the same time as an irrigation attachment piece 30 for the introduction of cleaning liquid. For this purpose, the first latching mechanism 29 is also designed as a coupling for attachment to a corresponding device of a medical irrigation machine. In this way, cleaning liquid can be introduced into the main lumen 3 and via the transition area 15 also into the secondary lumen 14 of the tube 2, such that contaminants are flushed out in the distal direction. Moreover, in the proximal end area, a second latching mechanism 31 is provided, with the aid of which the endoscopic instrument 1, when inserted into an outer shaft (see FIG. 5), can be fixed in a suitable position therein.

Figure 4:
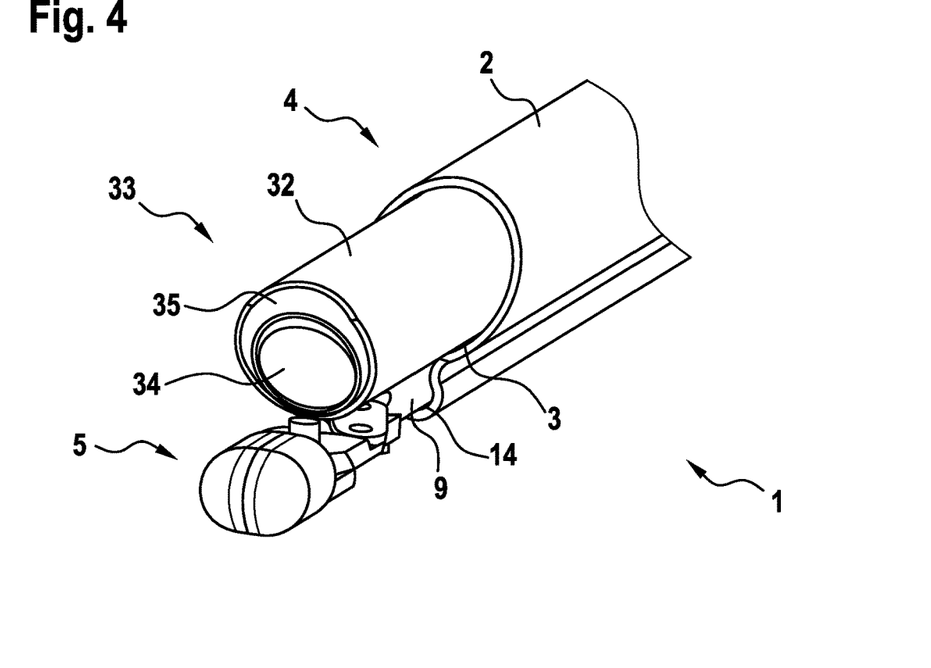
FIG. 4 shows the distal end area of the endoscopic instrument as in FIG. 2, but with an endoscope lens system inserted into the tube.

In FIG. 4, the distal end of the tube 2 of the endoscopic instrument 1 is shown as in FIG. 2, but with the shaft 32 of an endoscope lens system 33 inserted into the main lumen 3. The fork 10 (see FIG. 1) is not shown. As can be seen in FIG. 4, the distal end face of the shaft 32 of the endoscope lens system 33 comprises a light entry surface 34 of the optics of the endoscope lens system 33 and a light exit surface 35, in which the optical fibers of the light-guiding system for the illumination light open out. The endoscope lens system 33 comprises an eyepiece or a camera attachment, and also an attachment piece for illumination light, which are arranged at the proximal end of the shaft 32 and which remain outside the tube 2 (not shown). In the example shown in FIG. 4, the end face of the endoscope lens system 33 is inclined with respect to the longitudinal axis of the shaft 32, i.e. the endoscope lens system 33 is an oblique view optic. This allows the forceps 5 to be arranged favorably in the viewing field of the endoscope lens system 33, such that manipulations performed with the forceps 5 can be observed with the aid of the endoscope lens system 33. For this purpose, the shaft 32 of the endoscope lens system 33 is pushed slightly past the distal opening of the tube 2. In this position, the endoscope lens system 33 can be fixed in the tube 2 by means of the first latching mechanism 29 (see FIG. 3).

Figure 5:
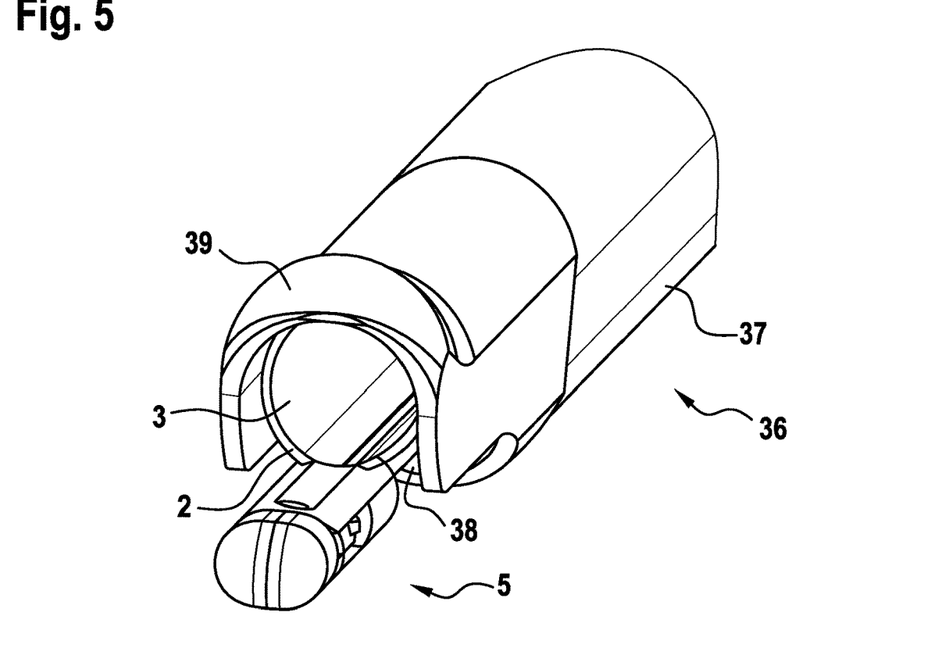
FIG. 5 shows the distal end area of the endoscopic instrument as in FIG. 1, but inserted into an outer tube.

In FIG. 5, the distal end area of the tube 2 is shown with the forceps 5 as in FIG. 1, but with the tube 2 inserted into an outer shaft 36. The outer shaft 36 comprises an elongate outer tube 37 which forms a continuous cavity for receiving the tube 2 and which has a cross section composed of two semicircles with straight parts lying between these. A space 38 remaining between the outer tube 37 and the tube 2 can be used, for example, for irrigating the operating site where the endoscopic manipulations are being performed with the forceps 5. A raised lip 39, which is rounded so as not to cause trauma, is mounted on the distal end of the outer tube 37 and serves to create a cavity for performing the endoscopic manipulations with the forceps 5 and for permitting a free view from the endoscope lens system as shown in FIG. 4, which endoscope lens system is not shown in FIG. 5. In a position suitable for this, the endoscopic instrument 1 can be fixed inside the outer shaft 36 by means of the second latching mechanism (see FIG. 3).

Figure 6:
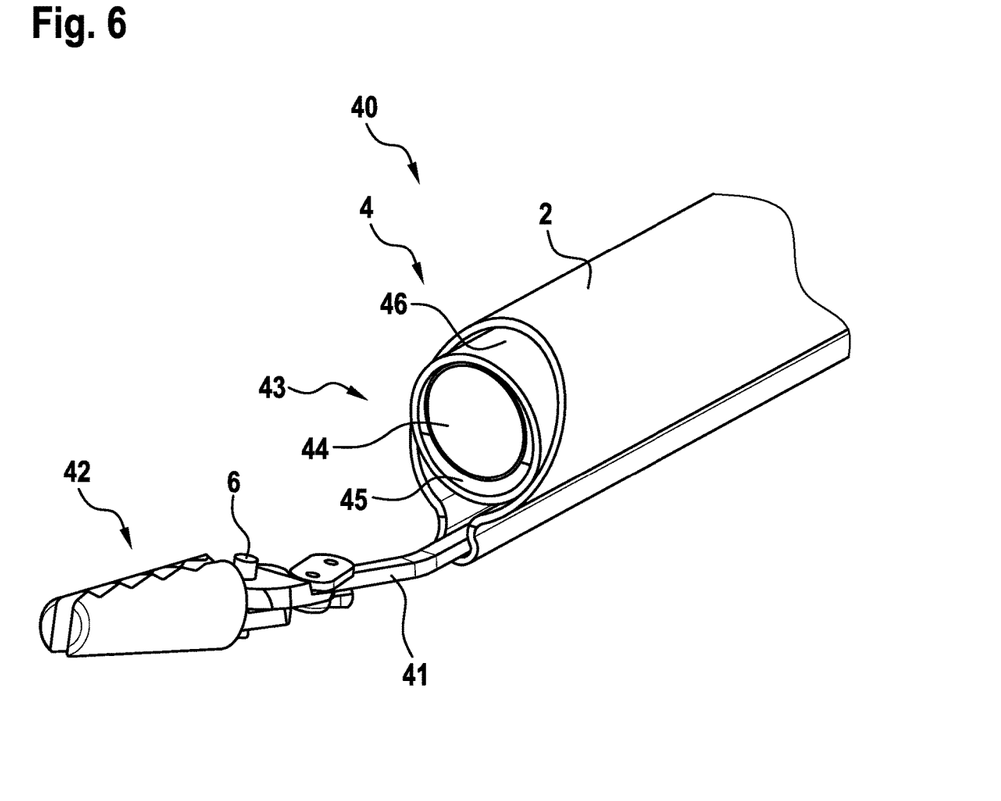
FIG. 6 shows an endoscopic instrument according to a second illustrative embodiment of the invention, in a view corresponding to FIG. 4.

FIG. 6 shows a second embodiment of the invention, with an endoscope lens system inserted into the tube 2 as in FIG. 4. In the endoscopic instrument 40 according to FIG. 6, the pull rod 41 is flattened and, in its distal end area, is angled upward with respect to the longitudinal axis of the tube 2, i.e. angled toward the longitudinal axis. This allows the tool, designed in FIG. 6 as gripping forceps 42, to come to lie near a central axis of the tube 2, such that it can be advantageously observed with an endoscope lens system 43 whose light entry surface 44 and light exit surface 45 are perpendicular to the longitudinal axis of the shaft 46 of the endoscope lens system 43 and thus designed as a straight-view optics system. Otherwise, the illustrative embodiment shown in FIG. 6 is like the one described above and shown in FIGS. 1 to 5. The holder, with which the transverse stub 6 is held on the distal end 4 of the tube 2, is not shown in FIG. 6.

For the sake of clarity, not all of the reference signs are shown in all of the figures. Reference signs that are not explained in connection with one figure have the same meaning as in the other figures.

What is claimed is:

1. An endoscopic instrument comprising: an elongate tube having an axially continuous and substantially cylindrical main lumen configured to receive a shaft of an endoscope lens system, a tool, which is arranged at a distal end of the tube and is connected to a distal end region of the tube, the tool having at least one movable tool element, and an elongate transmission element, the tool being controllable via the transmission element from a proximal end of the tube, the transmission element being a pull rod or pull wire, the tool element being movable about a transverse stub by the pull rod or pull wire, the transverse stub being connected to the distal end region of the tube by a holder, wherein the tube has an axially continuous secondary lumen, which is joined next to the main lumen in a direction transverse to a longitudinal axis of the tube, opens into the main lumen via a narrowed transition area, and receives the transmission element, the secondary lumen having a smaller cross-sectional area than the main lumen, wherein the narrowed transition area is narrower than a corresponding transverse dimension of the pull rod or pull wire, wherein the transition area provides passage between the main lumen and the secondary lumen, and wherein the secondary lumen of the tube is stiff and securely guides the transmission element when the transmission element is inserted into the secondary lumen.

2. The endoscopic instrument according to claim 1, wherein the tube is designed with a substantially uniform wall thickness.

3. The endoscopic instrument according to claim 2, wherein the narrowed transition area is axially continuous.

4. The endoscopic instrument according to claim 1, wherein the narrowed transition area is axially continuous.

5. The endoscopic instrument according claim 1, wherein the transmission element is guided at a distance from the shaft of the endoscope lens system inserted into the main lumen.

6. The endoscopic instrument according to claim 1, wherein the transmission element is guided in the secondary lumen with a clearance such that there is a distance between the transmission element and an inner wall of the tube, the distance providing passage of fluid for irrigation of the secondary lumen.

7. The endoscopic instrument according to claim 6, wherein the distance between the transmission element and the inner wall of the tube is on an order of tenths of a millimeter.

8. The endoscopic instrument according to claim 1, wherein the tool is designed as forceps or scissors and comprises at least one forceps or scissor part which is pivotable about the transverse stub.

9. The endoscopic instrument according to claim 1, wherein a proximal end area of the tube has an attachment piece for introduction of a cleaning liquid into the main lumen and into the secondary lumen through the narrowed transition area.

10. The endoscopic instrument according to claim 1, wherein at the distal end of the tube, the main lumen has an opening which is configured oblique relative to the longitudinal axis of the tube.

11. The endoscopic instrument according to claim 1, wherein at the distal end of the tube, the secondary lumen has an opening which is configured perpendicular relative to the longitudinal axis of the tube.

12. The endoscopic instrument according to claim 1, wherein the tool is oriented towards the longitudinal axis of the tube, and wherein a distal end of the transmission element is angled towards the longitudinal axis of the tube.

13. The endoscopic instrument according to claim 1, further comprising a joint mechanism connecting the transmission element to the tool, and an enclosure enclosing the joint mechanism, the enclosure being secured to the distal end of the tube.

14. The endoscopic instrument according to claim 1, wherein the tube is configured to be inserted into an outer shaft and fixed to the outer shaft.

15. The endoscopic instrument according to claim 1, wherein the tube has a non-circular cross section perpendicular to the longitudinal axis of the tube as a result of the secondary lumen joined next to the main lumen.

16. An endoscopic instrument system comprising:
   an endoscopic instrument which includes:
      an elongate tube having an axially continuous and substantially cylindrical main lumen configured to receive a shaft of an endoscope lens system, and
      a tool, which is arranged at a distal end of the tube and is connected to a distal end region of the tube, the tool having at least one movable tool element, and
      an elongate transmission element, the tool being controllable via the transmission element from a proximal end of the tube, the transmission element being a pull rod or pull wire, the tool element being movable about a transverse stub by the pull rod or pull wire, the transverse stub being connected to the distal end region of the tube by a holder,
      the tube having an axially continuous secondary lumen, which is joined next to the main lumen in a direction transverse to a longitudinal axis of the tube, opens into the main lumen via a narrowed transition area, and receives the transmission element, the secondary lumen having a smaller cross-sectional area than the main lumen,
      the narrowed transition area being narrower than a corresponding transverse dimension of the pull rod or pull wire,
      the transition area providing passage between the main lumen and the secondary lumen,
      the pull rod or pull wire is disposed in the secondary lumen; and
   a rigid endoscope lens system configured to be inserted into the main lumen of the tube of the endoscopic instrument.

17. The endoscopic instrument system according to claim 16, further comprising an outer shaft configured to receive the endoscopic instrument, wherein the outer shaft has a length such that the tool of the endoscopic instrument protrudes from a distal opening of the outer shaft.

18. An endoscopic instrument comprising: a proximal end and a distal end; a handle at the proximal end; an elongate tube extending from the distal end to the handle, the tube having a cavity which extends along a longitudinal axis of the tube, the cavity being formed by a main lumen, a secondary lumen, and a transition area between the main lumen and the secondary lumen, the transition area comprising a constriction in a wall of the tube and providing passage between the main lumen and the secondary lumen, the secondary lumen having a smaller cross-sectional area than the main lumen, the tube being designed with a substantially uniform wall thickness; a tool arranged at a distal end of the tube and connected to a distal end region of the tube, the tool having at least one movable tool element; an elongate transmission element connected to the tool, wherein the tool is controlled by the handle via the transmission element, the transmission element being a pull rod or pull wire, the tool element being movable about a transverse stub by the pull rod or pull wire, the transverse stub being connected to the distal end region of the tube by a holder, the pull rod or pull wire being disposed in the secondary lumen; a latch disposed at a proximal end region of the tube, the latch being configured to lock an endoscope lens system to the tube when a shaft of the endoscope lens system is received in the main lumen; wherein the transition area is narrower than a corresponding transverse dimension of the pull rod or pull wire; wherein the latch includes an irrigation attachment piece which provide fluids connection to an irrigation machine to introduce a liquid into the main lumen and the secondary lumen.

\* \* \* \* \*